United States Patent [19]
Ricoux et al.

[11] Patent Number: 6,128,544
[45] Date of Patent: Oct. 3, 2000

[54] PROCESS FOR MONITORING AND CONTROL OF THE OPERATION OF AN ANALYZER AND OF A MANUFACTURING UNIT TO WHICH IT IS LINKED

[75] Inventors: Philippe Ricoux, Brignais; Claude Alain Saby, Bron, both of France

[73] Assignee: Elf Antar France, Courbevoie, France

[21] Appl. No.: 08/732,117

[22] Filed: Oct. 15, 1996

[30] Foreign Application Priority Data

Oct. 16, 1995 [FR] France ................................. 95 12087

[51] Int. Cl.⁷ ................................................. G06F 19/00
[52] U.S. Cl. ............................... 700/110; 700/108; 700/3
[58] Field of Search ............................... 700/108, 3, 110, 700/89, 187

[56] References Cited

U.S. PATENT DOCUMENTS

| | | | |
|---|---|---|---|
| 5,008,842 | 4/1991 | Nagai et al. | 702/183 |
| 5,191,521 | 3/1993 | Brosilow | 364/160 |
| 5,206,937 | 4/1993 | Goto | 709/209 |
| 5,327,349 | 7/1994 | Hoste | 364/468.17 |
| 5,442,562 | 8/1995 | Hopkins et al. | 364/468.15 |
| 5,708,593 | 1/1998 | Saby et al. | 702/85 |
| 5,715,181 | 2/1998 | Horst | 702/180 |

*Primary Examiner*—William Grant
*Assistant Examiner*—Zoila Cabrera
*Attorney, Agent, or Firm*—Oblon, Spivak, McClelland, Maier & Neustadt, P.C.

[57] ABSTRACT

A process for monitoring and controlling a slave analyzer and a manufacturing unit linked to the slave analyzer, including the steps of a) feeding standard samples having a known characteristic to a master analyzer; b) generating master signals from the master analyzer based on the known characteristic of the standard samples; c) feeding the standard samples to the slave analyzer; d) generating slave signals from the slave analyzer based on the known characteristic of said standard samples; e) generating a transfer algorithm relating the slave signals to the master signals, the transfer algorithm being defined by parameters; f) periodically repeating steps c) through e); g) monitoring over time an indicator selected from the group consisting of one of the parameters and a function of at least two of the parameters; h) identifying a cause of alteration of the indicator based on a cause/effect diagram; and i) checking the slave analyzer and the manufacturing unit based on the cause of alteration of the indicator.

11 Claims, No Drawings

PROCESS FOR MONITORING AND CONTROL OF THE OPERATION OF AN ANALYZER AND OF A MANUFACTURING UNIT TO WHICH IT IS LINKED

TECHNICAL FIELD

The present invention relates to a process for monitoring and control of the operation of an analyser and of the operation of a manufacturing unit to which it is linked.

It finds its application in control laboratories, research laboratories, manufacturing units in the chemical, petroleum, pharmaceutical, cosmetological and farm-produce industries.

PRIOR ART

Numerous analysers such as spectrometers used to determine the physical or chemical characteristics of a sample of product to be analysed require calibration.

This calibration consists in establishing a model which represents the mathematical relation between a characteristic of the product to be analysed and the signal delivered by the analyser.

This operation is lengthy and requires the use of several tens of products, whose characteristics have been determined by direct measurements.

This operation having been performed on a given analyser termed the master analyser, it is of particular benefit to use the model thus obtained on one (or more) other analyser(s) of the same kind termed the slave analyser(s), so as to avoid having to repeat the calibration operations several times with these apparatuses.

In order to take account of the differences in instrument responses between the master analyser and the slave analyser which alter over time for example as a function of the conditions of operation and the ageing of the components of the slave analyser, the signals delivered by the slave analyser are corrected by subjecting them to periodic standardization operations.

In order to perform these standardization operations, several methods may be employed.

By way of example there may be mentioned the method of SHENCK which is described in the U.S. Pat. No. 4,866,644 and the method described in French Patent Application No. 95 05957.

All these methods include a number of steps during which calibration transfer parameters are calculated which culminate in the calculation of the correction of the signals from the slave analyser.

None of these methods allows identification of the origin of the drifts, malfunctions, disturbances throughout the analysis chain, nor do they enable the user to be warned of the appearance of phenomena which may lead to erroneous results despite the correction afforded by the standardization, the latter being valid only within a given range of operation of the slave analyser and within the limits of validity of the calibration model.

These methods give no indication regarding the operation of the manufacturing units to which the analysers are linked. In order to perform the monitoring and control of a manufacturing unit a known method consists in employing multivariate control charts which require the ascertaining of numerous variables characteristic of the operation of the manufacturing process. In numerous cases these variables are not measurable or are not measured for technical and/or economic reasons.

Moreover, the monitoring and control criteria are difficult to determine.

ACCOUNT OF THE INVENTION

The precise object of the present invention is to remedy these drawbacks, and in particular to provide a process for monitoring and control of the operation of a slave analyser and of the manufacturing unit to which it is linked.

By virtue of this process, it is possible to reveal disturbances, drifts, anomalies of operation of the slave analyser and of the associated measurement chain including the manufacturing unit to which it is linked, to identify the causes of these malfunctions and to make provisions suited to each situation: for example to declare the result of the analysis invalid and warn the operator utilizing the unit to which the analyser is linked and furnish him with the elements in order to make his decisions.

This process finds its application in analysis laboratories and manufacturing units.

For this purpose the present invention proposes a process for monitoring and control of the operation of a slave analyser and of a manufacturing unit to which it is linked, characterized in that it comprises an operation of multivariate calibration of a master analyser, periodic operations of standardizing signals delivered by the slave analyser fed with standardizing products and a calibration transfer step during which parameters associated with a calibration transfer algorithm are calculated, and in that, on the one hand, one of the said parameters or a mathematical combination of at least two of them is chosen as monitoring and control indicator of the operation of the slave analyser and, on the other hand, a method of monitoring and control is chosen, and in that on completion of each periodic standardization operation the alteration over time of the value of the monitoring and control indicator is logged by applying the method of monitoring and control, then the proper operation of the slave analyser and that of the manufacturing unit to which it is linked are checked by identifying the causes of the alteration of the value of the indicator from the results obtained by applying the method of monitoring and control and a cause/effect diagram.

According to another characteristic of the invention the slave analyser and the master analyser are the same analyser used at different periods of time.

According to another characteristic of the invention after detecting a significant drift of the monitoring and control indicator, the validity of the results from the master analyser is checked by regarding it as the slave analyser.

According to another characteristic of the invention, during the standardization operations consisting, for at least one of them, on the one hand in decomposing in series the signals delivered by the master and slave analysers, and on the other hand in establishing a mathematical relation between the coefficients from the series decompositions, one of the parameters calculated in order to define the said mathematical relation or a mathematical combination of at least two of the said parameters is chosen as monitoring and control indicator.

According to another characteristic of the invention, during the standardization operations consisting, for at least one of them, on the one hand in decomposing in series the signals delivered by the master and slave analysers, and on the other hand in establishing a mathematical relation between the coefficients from the series decompositions, the said mathematical relation being represented by neural networks, one of the parameters calculated in order to define the neural networks or a mathematical combination of at least two of the said parameters is chosen as monitoring and control indicator.

According to another characteristic of the invention, during the standardization operations, at least one of which involves a matrix calculation of coefficients, a matrix of coefficients arising from the said calculation or a combination of at least two matrices of the said coefficients is chosen as monitoring and control indicator.

According to another characteristic of the invention the monitoring and control method employs at least one monovariate control chart.

According to another characteristic of the invention the monitoring and control method employs at least one multidimensional control chart.

According to another characteristic of the invention the monitoring and control method employs at least one neural network.

According to another characteristic of the invention, when the standardization operations employ at least two different standardization techniques, the cause/effect diagram is constructed from the coefficients arising from at least two of the said techniques.

According to another characteristic of the invention the signals delivered by the master and slave analysers are subjected beforehand to operations of differentiation with respect to time.

DETAILED ACCOUNT OF THE INVENTION

In a general way the process of the invention makes it possible to monitor and control the operation of a slave analyser linked to a manufacturing unit or the operation of a laboratory analyser.

The invention will be better understood with the aid of the following description of two embodiments given by way of non-limiting examples.

According to a first embodiment, the master and slave analysers are infrared spectrometers which measure absorbances in the range of wavelengths from 1076 to 1548 nm.

The master analyser is a laboratory spectrometer and the slave analyser a spectrometer linked to a hydrocarbon processing unit, in order to determine a characteristic of fuels intended for powering internal combustion engines.

The process of the invention consists in supplementing the known operations of calibration and standardization of the signals with operations for monitoring and control of the slave analyser.

The calibration operations consist in establishing a model from each of the signals arising from the analysis by the master analyser of each fuel of a set of calibration fuels, for which the value of the sought-after characteristic is known.

The model represents the mathematical relation between the value of the characteristic of the fuel analysed and the signal delivered by the master analyser.

Since this model is to be used on other analysers and in order to take account of the differences in instrument responses between the master and slave analysers, as well as drifts over time of the slave analyser, several methods propose correcting the signal delivered by the slave analyser. The operations for performing these corrections are known by the name of calibration transfer operations.

They consist firstly in calculating, as will be seen later, coefficients for correcting the signal and in storing them in the form of a transfer matrix. The latter is next used to correct each signal delivered by the slave analyser for each sample of fuel for which it is desired to ascertain the value of the characteristic.

The correction coefficients are calculated as follows:

10 samples of standardization fuels representative of the population of the fuels to be analysed are selected, for example, for which the value of the characteristic is known.

The master and slave analysers are each fed with these fuels, and each deliver a signal for each sample.

A FOURIER series decomposition of each signal delivered by each of the analysers is performed.

For each sample of standardization fuel the Fourier transform of the signal is expressed by the following formula:

$$F(k) = \frac{1}{N}\sum_{i=0}^{N-1} y_i \exp\left(-j2i\pi\frac{k}{N}\right)$$

in which:
the $y_i$ are the values of a signal decomposed into N points,
i varies from 0 to N-1
k varies from 0 to N-1
the F(k) are the values resulting from the Fourier transform at the frequency k/N; however, it is not necessary to use the complete Fourier transform but merely the first n values of F(k) with k lying between 0 and n, n being very small compared with N-1.

The value of n is determined through a stop criterion reflecting the convergence between the signal recomposed by inverse Fourier transform and the true signal from at least one of the standardization fuels.

For this signal the coefficients n lying between 20 and 40 are selected and then the signal is recomposed with these n coefficients.

Next, the square root (RSD) of the sum of the squares of the differences between the absorbance values for each wavelength, and the mean (ME) of the standard deviations, are calculated. The first differences ($\Delta 1R$) of the RSDs and then the second differences ($\Delta 2R$) are calculated from these values, this giving a table such as the following:

| n  | ME   | $\Delta 1R$ | $\Delta 2R$ |
|----|------|-------------|-------------|
| 30 | 0.81 | —           | —           |
| 31 | 0.64 | 0.17        | —           |
| 32 | 0.52 | 0.12        | 0.05        |
| 33 | 0.43 | 0.09        | 0.03        |
| 34 | 0.34 | 0.09        | 0.          |
| 35 | 0.32 | 0.02        | 0.07        |
| 36 | 0.20 | 0.12        | −0.10       |
| 37 | 0.17 | 0.03        | 0.09        |
| 38 | 0.12 | 0.05        | −0.02       |

Cattel's criterion is adopted as stop criterion, corresponding to a reversal of sign of $\Delta 2R$, this giving the value n=35 in our example.

Thus, for each signal, two series of coefficients of the Fourier transform are obtained:
the real coefficients $r_1, r_2, \ldots r_{35}$
the imaginary coefficients $k_1, k_2, \ldots k_{35}$
A linear relation such as:

$$\hat{B} = \alpha + \beta A$$

is chosen as mathematical relation between the coefficients thus obtained, in which relation:

A represents the matrix of coefficients obtained via the Fourier transform of the signals delivered by the master analyser.

$\hat{B}$ represents the matrix of coefficients estimated in the least squares sense of the Fourier transform of the signals from the slave analyser.

$\alpha$ and $\beta$ are respectively the matrices of slope coefficients and of ordinate coefficients at the origin, estimated via the least squares algorithm. $\alpha$ and $\beta$ define the transfer matrix.

The signals from the products analysed on the slave analyser are recomposed by means of the inverse Fourier transform, from their estimated coefficients.

The transfer matrix is validated by comparing the signals from the products analysed on the master analyser with the corrected signals from the same products analysed on the slave analyser according to two methods:

The standard deviations of the respective RSDs are calculated.

The calibration model is applied to the signals from the master analyser and to the signals from the slave analyser. The values, obtained respectively with the two analysers, of the characteristic investigated are compared and then the degree of significance of the standard deviations observed is tested.

If the results of the calculation of the RSDs exceed an experimentally determined value or if the values of the standard deviations observed via the second method are too high, the previous steps are repeated, modifying the calculation hypotheses until convergence is obtained.

Every signal obtained on the slave analyser fed with a product whose characteristic is sought is decomposed into a Fourier series. The value of n is calculated for this signal according to the same criterion as that chosen previously. A positive or negative difference of 2 between the value of n determined by this signal and that obtained previously indicates an anomaly, the causes of which will be sought in a later step.

If no anomaly is detected, the decomposed signal from the slave analyser is recomposed from the coefficients corrected by the transfer algorithm. Next the calibration model determined on the master instrument is applied to the recomposed signal from the slave instrument in order to obtain the sought-after characteristic.

In order to monitor and control the operation of the slave analyser or that of the manufacturing unit to which it is linked, univariate control charts are used.

Each chart monitors the alteration of a parameter, for example: the number n, the coefficients $\alpha$ and/or $\beta$, the RSDs. A monovariate chart is also used to monitor the alteration of the sought-after characteristic arising from the model as result from the transfer algorithm.

Multivariate charts can also be used to carry out a principal components analysis (PCA) on the values of the coefficients $\alpha$ and $\beta$ which constitute the transfer matrix.

The limit values of the control and monitoring parameter or parameters are determined experimentally especially as a function of the permissible range of alteration of the sought-after characteristic.

If the value or values of the control and monitoring parameter or parameters are within the previously determined limits, the analysis procedure is continued.

Otherwise, the exceeding of the limit values is characteristic of an anomaly whose cause will have to be sought in the next step.

If the values of a monitoring parameter remain within the determined limits, but these values alter in a non-random manner (for example linearly over time), monitoring rules adapted to the problem detected and to the parameter monitored must be defined.

The causes of shifting are analysed by employing a method of cause/effect type, by virtue of which the causes are identified of the anomalies detected, for example the quality of the product analysed, the operation of the master or slave analysers, the calibration model, the transfer algorithm, or the malfunction of the manufacturing unit to which the slave analyser is linked.

EXAMPLE 2

According to a second embodiment of the invention, the mathematical relation chosen in the first embodiment, $\hat{B}=\alpha+\beta A$, is replaced by a relation based on neural networks.

According to the second embodiment, a gradient retro-propagation network with architecture 35-4-35 is chosen.

This architecture yields a number of weights of 319.

The number of values of the transfer matrix is equal to 35×10, i.e. 350. In our example the number of signals taken into account in computing the transfer matrix equal to 10 is a lower limit number if reference is made to a mode of calculation generally used.

The alteration is monitored over time of the parameters of the transfer matrix or of the parameters which served for its computation, by monitoring the number of neurons in the hidden layer and/or the alteration of the weights and of their distance with regard to experimentally determined thresholds.

A table of defects is established, the monitoring of all the elements of which makes it possible to discern alterations in the manufacture of the products, to detect drifts in this manufacture over time, to detect the presence of particular products and the existence of disturbances other than those connected with the apparatuses.

What is claimed as new and desired to be secured by Letters Patent of the United States is:

1. A process for monitoring and controlling a slave analyser and a manufacturing unit linked to said slave analyser, comprising the steps of:

a) feeding standard samples having a known characteristic to a master analyser;

b) generating master signals from said master analyser based on said known characteristic of said standard samples;

c) feeding said standard samples to said slave analyser;

d) generating slave signals from said slave analyser based on said known characteristic of said standard samples;

e) generating a transfer algorithm relating said slave signals to said master signals, said transfer algorithm being defined by parameters;

f) periodically repeating c) through e);

g) monitoring over time an indicator selected from the group consisting of one of said parameters and a function of at least two of said parameters;

h) identifying a cause of alteration of said indicator based on a cause/effect diagram; and i) checking said slave analyser and said manufacturing unit based on said cause of alteration of said indicator.

2. The process according to claim 1, wherein the slave analyser and the master analyser are one analyser used at different periods of time.

3. The process according to claim 1 or 2, further comprising checking the master analyser by treating said master analyser as the slave analyser.

4. The process according to claim 1, wherein generating said transfer algorithm comprises:
- decomposing in series the signals delivered by the master and slave analysers, and
- establishing a mathematical relation between coefficients from the series, said mathematical relation being defined by said parameters.

5. The process according to claim 1, wherein generating said transfer algorithm comprises:
- decomposing in series the signals delivered by the master and slave analysers, and
- establishing a mathematical relation between coefficients from the series, said mathematical relation being represented by neural networks defined by said parameters.

6. The process according to claim 1, wherein:
- generating said transfer function comprises performing a matrix calculation of coefficients, and
- said parameters are matrices of coefficients arising from the said matrix calculation.

7. The process according to claim 1, further comprising monitoring an alteration of a sought characteristic with at least one monovariate control chart.

8. The process according to claim 1, further comprising carrying out a principal component analysis of said parameters with at least one multidimensional control chart.

9. The process according to claim 1, wherein generating said transfer algorithm comprises generating at least one neural network.

10. The process according to claim 1, wherein:
- generating said transfer algorithm comprises applying at least two different standardization techniques, and further comprising
- constructing the cause/effect diagram from coefficients arising from at least two of the said standardization techniques.

11. The process according to claim 1, further comprising differentiating with respect to time the signals delivered by the master and slave analysers.

* * * * *